United States Patent [19]

Van Leeuwen et al.

[11] Patent Number: 5,004,844

[45] Date of Patent: Apr. 2, 1991

[54] PROCESS FOR THE REDUCTION OF CARBONYL COMPOUNDS

[75] Inventors: Petrus W. N. M. Van Leeuwen; Cornelis F. Roobeek, both of Amsterdam, Netherlands

[73] Assignee: Shell Oil Company, Houston, Tex.

[21] Appl. No.: 372,577

[22] Filed: Jun. 28, 1989

[30] Foreign Application Priority Data

Jun. 28, 1988 [GB] United Kingdom ................. 8815328

[51] Int. Cl.$^5$ ..................... C07C 29/14; C07C 29/132
[52] U.S. Cl. ..................... 568/880; 568/814; 568/876; 568/878; 568/884; 568/885
[58] Field of Search ............... 568/876, 880, 881, 884, 568/885, 814, 876, 880, 878

[56] References Cited

U.S. PATENT DOCUMENTS

| | | | |
|---|---|---|---|
| 3,574,716 | 4/1971 | Coffey | 568/881 |
| 3,968,147 | 7/1976 | Bolodar | 568/881 |
| 4,072,720 | 2/1978 | Haag et al. | 260/618 |
| 4,418,227 | 11/1983 | Pez et al. | 568/861 |

FOREIGN PATENT DOCUMENTS 1529619 10/1978 United Kingdom .
2054592  2/1981 United Kingdom ................ 568/881

OTHER PUBLICATIONS

P. W. N. M. van Leeuwen et al, Journal of the Chemical Soc., Chem. Comm., No. 1 (1986), pp. 31–33.
W. B. Beaulieu et al, Inorganic Chemistry, vol. 14, No. 7 (1975), pp. 1732–1734.
P. C. Kong et al, J. Chem. Soc., Dalton Trans., vol. 2 (1974), pp. 187–189.

*Primary Examiner*—Werren B. Lone

[57] ABSTRACT

A process for the preparation of a primary or secondary alcohol, which comprises hydrogenating respectively an aldehyde or ketone in the presence of a catalyst system comprising a platinum compound, an acid having a pKa in the range from about 2 to about 10.5 and a phosphorus compound of the formula $R^1R^2POH$, wherein $R^1$ and $R^2$ each independently represents an alkyl group or a phenyl group, at a temperature in the range from about 20° to about 150° C. and at a pressure in the range from about 1 to about 100 bar.

25 Claims, No Drawings

PROCESS FOR THE REDUCTION OF CARBONYL COMPOUNDS

FIELD OF THE INVENTION

The present invention relates to a process for the preparation of primary or secondary alcohols by the reduction of aldehydes or ketones. In particular, it relates to a hydrogenation process promoted by a homogeneous catalyst system comprising a platinum compound, a phosphorus compound, and an acid.

P.W.N.M. van Leeuwen et al (J. Chem. Soc., Chem. Commun., 1986, 31 to 33) describe the hydroformylation of certain alkenes using a catalyst system comprising a platinum compound and a phosphorus compound of the formula $Ph_2POH$. The products of the hydroformulation are mixtures of aldehydes or ketones and alcohols. Presumably, the alcohols in that product mixture are formed by the hydrogenation of carbonyl compounds.

SUMMARY OF THE INVENTION

It has now been found that aldehydes and ketones can advantageously be hydrogenated using a catalyst system comprising a platinum compound, a phosphorus compound, and an acid.

Accordingly, the present invention provides a process for the preparation of primary and secondary alcohols, which comprises contacting and reacting hydrogen with a carbonyl reactant comprising one or more compounds selected from the group consisting of aldehydes and ketones in the presence of a catalyst system comprising a platinum compound, an acid having a pKa in the range from about 2 to about 10.5 and a phosphorus compound of the formula $$R^1R^2POH \quad \quad (I)$$

in which $R^1$ and $R^2$ each independently represents an alkyl group or a phenyl group, at a temperature in the range of from about 20 to about 150° C. and a pressure in the range of from about 1 to about 100 bar. Hydrogenation of an aldehyde yields the corresponding primary alcohol, while hydrogenation of a ketone yields the corresponding secondary alcohol.

The process of the invention has particular advantage in producing alcohols at a very high reaction rate.

Description of the Preferred Embodiments

Preferably the aldehyde or ketone utilized as starting material in the process of the invention is a compound of the formula

$$R^3CHO \quad \quad (II)$$

$$or \ R^3COR^4 \quad \quad (III)$$

in which each of $R^3$ and $R^4$ is independently selected the group consisting of alkyl, alkenyl, aryl, cycloalkyl and cycloalkenyl moieties and moieties wherein $R^3$ and $R^4$ together form an alkylene chain which may contain one or more carbon-carbon double bonds. Each of such $R^3$ and $R^4$ groups may further suitably contain other substituents (e.g., preferably one or more substituents selected from the group consisting of alkyl, alkoxy and alkoxyalkyl groups) which are essentially inert in the process of the invention, although unsubstituted hydrocarbyl $R^3$ and $R^4$ groups are preferred.

Alkyl and alkenyl groups preferably have from 1 to about 10, more preferably from about 3 to about 7 carbon atoms. Each aryl group is preferably a phenyl group. Any cycloalkyl or cycloalkenyl group preferably has from 5 to 7 carbon atoms. An alkylene chain formed by the joining of $R_3$ and $R_4$ and having one or more carbon-carbon double bonds preferably has from 4 to 6 carbon atoms.

Very surprisingly, it has been found that when aldehyde or ketone compounds containing a non-conjugated carbon-carbon double bond are hydrogenated according to the process of the invention, the carbon-carbon double bond is remarkably resistant to reduction. Accordingly, the process according to the invention is particularly advantageous for the selective reduction of carbonyl reactants containing one or more aldehydes and/or ketones containing a non-conjugated carbon-carbon double bond.

It is particularly surprising that aldehydes can be successfully reduced to the corresponding alcohols by the process according to this invention. Ruthenium and rhodium based catalysts can be poisoned by carbon monoxide which may be liberated during such a hydrogenation process.

The catalyst system used in the process according to the invention may be generated by mixing each of the individual components. Alternatively, the catalyst system can be generated by mixing substances which do not correspond to each of the individual components, but which in combination generate the catalyst system.

The platinum compound may, conveniently, be a salt of platinum, preferably an organic salt, for example, a platinum carboxylate such as acetate, or a complex of platinum, for example platinum bis(cyclo-octa-1,5diene) or platinum tris(ethylene).

The acid having a pKa in the range of from about 2 to about 10.5 may be an inorganic acid such as phosphoric acid or an organic acid such as a carboxylic acid or phenol. Preferably the acid is a carboxylic acid.

When the acid having a pKa in the range of from about 2 to about 10.5 is a carboxylic acid, it may be an aliphatic carboxylic acid such as an alkanoic acid, e.g., ethanoic acid, propanoic acid, butanoic acid or 2-methylpropanoic acid., or an aromatic carboxylic acid such as benzoic acid.

For the phosphorus compound of formula (I), $R^1$ is preferably a $C_1$ to $C_{10}$ alkyl group or a phenyl group. The phenyl group may suitably contain alkyl substituents and/or other substituents which do not interfere with the function of the catalyst component. Particularly preferred are compounds wherein both $R^1$ and $R^2$ groups are phenyl groups; diphenylphosphinous acid is considered most preferred.

The process according to the invention is suitably effected at a temperature in the range from about 20° C. to about 150° C., and preferably in the range from about 80 to about 120° C.

The process is suitably conducted at a partial pressure of hydrogen in the range from about 1 to about 100 bar, preferably in the range from about 20 to about 60 bar.

The molar ration of the phosphorus compound of formula (I) to the platinum compound is conveniently in the range from about 1:1 to about 4:1, but could be higher. Preferably, this ratio is in the range of from about 2:1 to about 4:1.

In generating the catalyst system, the platinum compound and the phosphorus compound of formula (I) may be introduced separately or, alternatively, in the form of a single complex. For example, these two catalyst system components may be introduced in the form of a single complex of the formula $$(R^1R^2PO)(R^1R^2POH)_2PtH \qquad (IV)$$

in which $R^1$ and $R^2$ have the same meanings which they are assigned for formula (I). For this particular complex, the molar ratio of phosphorus compound to platinum compound is, of course, 3:1.

The molar ratio of the acid having a pKa in the range from about 2 to about 10.5 to the platinum compound may conveniently be in the range from about 1:1 to about 100:1.

It will be appreciated that aldehydes tend to react with air to afford carboxylic acids. Consequently impure samples of aldehydes may contain carboxylic acids. The presence of such acids in aldehyde reactants should be taken into account when creating the catalyst system of the invention. The acids present in such an impure aldehyde feedstock may serve, at least in part, as the acid component of the catalyst system.

The process may, if desired, be carried out in the presence of a solvent. However, a the use of a solvent is not necessary to the process. Examples of suitable solvents include aromatic hydrocarbons such as toluene; haloalkanes such as dichloromethane., ethers such as dioxane and tetrahydrofuran; esters such as ethyl ethanoate, and alcohols such as ethanol.

In certain cases, it is advantageous to use an additional pi-acceptor ligand in the catalyst system. The additional pi-acceptor ligand may be, for example, carbon monoxide, ethane, triphenylphosphine, tri(p-tolyl)-phosphine or tricyclohexylphosphine. Additional gaseous pi-acceptor ligands may conveniently be present at a molar ratio of phosphine to platinum of less than about 2.

The alcohol products of the process according to the invention may be recovered using techniques well known in the art of homogeneous catalysis, such as distillation under reduced pressure. Advantageously, platinum may be recovered from the reaction product by chromatography over phosphine-carrying resins, and the phosphine oxides may be removed by percolation over alumina.

The following examples are intended to illustrate certain preferred embodiments of the invention, without limiting its broader scope.

Example 1

Hydrogenation of
3-(4-Methyl-3-cyclohexen-1-yl)-1-butanal

A 100ml autoclave (Hastelloy C) was charged with 20ml of toluene, 15 mmol of 3-(4-methyl-3-cyclo-hexen-1-yl)butanal, 0.05 mmol of $(Ph_2PO)(PH_2POH)_2PtH$ and 0.5 mmol of $CH_3COOH$. (The aldehyde had been prepared by the hydroformylation of limonene, as described in published European patent application 54,986.) The autoclave was then pressurized with 40 bar $H_2$ and then heated to 95° C. The reaction mixture was kept at this temperature for 0.5 hours. The mixture was then allowed to cool and was analyzed thereafter using gas-liquid chromatography. Conversion of 3-(4-methyl-3-cyclohexen-1-yl)butanal was 37.5%, with a selectivity to 3-(4-methyl-3-cyclohexen-1-yl)-1-butanol of 90%. Less than 10% of the olefinic double bond had been hydrogenated. From the conversion, amount of catalyst and the reaction time, an average turnover per hour was calculated to be 200 mol of product per mol of catalyst per hour.

Examples 2 to 11

The procedures of Example 1 were repeated using different aldehyde or ketone starting material The amounts of substances used and the rates of reaction are given in Table 1. The rate indicated is an average rate in mol product per mol of catalyst per hour measured over 30–50% conversion.

TABLE 1

| Example Number | $(Ph_2POH)_3Pt$ (mmol) | Acid (mmol) | Additional Ligand(s) (bar) | Substrate (mmol) | Solvent (ml) | Product | Rate $m \cdot m^{-1} \cdot h^{-1}$ |
|---|---|---|---|---|---|---|---|
| 2* | 0.02 | $(CH_3)_2CHCOOH$ (4) | none | $(CH_3)_2CHCHO$ (110) | Ethanol (20) | i-butanol $(CH_3)_2CHCH_2OH$ | 1000 |
| 3* | 0.02 | $(CH_3)_2CHCOOH$ (4) | $C_2H_4$ (5) | $(CH_3)_2CHCHO$ (110) | Ethanol (20) | $(CH_3)_2CHCH_2OH$ | 2500 |
| 4 | 0.02 | $(CH_3)_2CHCOOH$ (4) | $C_2H_4$ (5) | $(CH_3)_2CHCHO$ (110) | Toluene (20) | $(CH_3)_2CHCH_2OH$ | 4500 |
| 5* | 0.01 | $(CH_3)_2CHCOOH$ | none | $(CH_3)_2CHCHO$ | none | $(CH_3)_2CHCH_2OH$ | 9000 |
| 6 | 0.02 | $CH_3COOH$ (0.1 | none | $(CH_3)_2CHCHO$ (22) | Toluene (20) | $(CH_3)_2CHCH_2OH$ | 1500 |
| Comparison | 0.02 | none | none | $(CH_3)_2CHCHO$ (22) | Toluene (20) | $(CH_3)_2CH_2CH_2OH$ | 200 |
| 7 | 0.02 | $CH_3COOH$ (10) | none | $CH_3COCH_3$ (275) | none | $(CH_3)_2CHOH$ | 500 |
| Comparison | 0.01 | none | none | $CH_3COCH_3$ | none | $(CHphd\ 3)_2CHOH$ | <10 |
| 8 | 0.02 | $(CH_3)_2CHCOOH$ (4) | none | Cyclohexanone (200) | none | Cyclohexanol | 1200 |
| 9 | 0.01 | $(CH_3)_2CHCOOH$ (5) | none | $(CH_3)_2CHCHO$ (220) | none | $(CH_3)_2CHCH_2OH$ | 2800 |
| 10 | 0.01 | $(CH_3)_2CHCOOH$ (5) | CO (5) H2 (35) | $(CH_3)_2CHCHO$ (220) | none | $(CH_3)_2CHCH_2OH$ | 1100 |
| 11 | 0.02 | 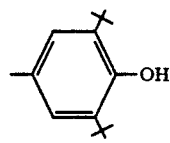 | none | $(CH_3)_2CHCHO$ | Toluene (20) | $(CH_3)_2CHOH$ | 220 |

TABLE 1-continued

| Example Number | (Ph$_2$POH)$_3$Pt (mmol) | Acid (mmol) | Additional Ligand(s) (bar) | Substrate (mmol) | Solvent (ml) | Product | Rate m · m$^{-1}$ · h$^{-1}$ |
|---|---|---|---|---|---|---|---|
| | | (0.1) | | | | | |

*Undistilled substrate; contained 4% (CH$_3$)$_2$CHCOOH.

Example 12

The method of Example 1 was repeated using 20.0 mmol of 5-formylbicyclo[2,2,1]-2-heptane (exo/endo, prepared by the Diels Alder addition of acrolein to cyclopentadiene) as the aldehyde, 0.05 mmol of (Ph$_2$PO)-(Ph$_2$POH)$_2$PtH and 1 mmol of PPh$_3$ as additional ligand. The reaction temperature was 110° C. The pressure applied was 38 bar of H$_2$ and 2 bar of CO. After 1 hour of reaction time 50% was converted to 5-hydroxmethyl-biclo-[2,2,1]-2-heptene with a selectivity of 98%. The calculated rate is 200 mol per mol per hour.

Examples 13 to 18

These examples show the effect of varying the presence and/or using additional pi-acceptor ligands on the hydrogenation of 5-formylbicyclo[2,2,1]-2-heptene. The amounts of reactants and solvent and the temperature were the same as in Example 12.

TABLE 2

| Example | PPh$_3$/ Pt Ratio | Bar H$_2$ | Bar CO | Bar C$_2$H$_4$ | Conv % | Sel % | Rate |
|---|---|---|---|---|---|---|---|
| 13 | | 40.00 | | | 90.00 | 50.00 | 400.00 |
| 14 | 1.00 | 20.00 | 20.00 | 10.00 | 10.00 | 98.00 | 40.00 |
| 15 | 2.00 | 40.00 | | | 25.00 | 65.00 | 100.00 |
| 16 | 1.00 | 40.00 | | | 50.00 | 60.00 | 200.00 |
| 17 | 1.00 | 20.00 | | | 45.00 | 65.00 | 180.00 |
| 18 | 1.00 | 38.00 | 2.00 | | 50.00 | 98.00 | 200.00 |

Example 19

10-decenal (5ml) was hydrogenated using 0.05 mmol of (Ph$_2$POH)-$_2$PtH, 25ml of toluene, and 0.5 mmol of isobutyric acid at a pressure of 40 bar H$_2$ and a temperature of 95° C. After 55 minutes the conversion was 56%, with a selectivity of 59% to the unsaturated aldehyde according to gas chromatographic analysis.

Example 20

The method of Example 19 was repeated but with (PPH$_2$OH)(PPh$_2$O)-PtH(P(p-tolyl$_3$)) as the platinum compound. The conversion was 63% after 70 minutes with a selectivity of 52%.

Example 21

The method of Example 20 was repeated but using a platinum compound of formula (PPh$_2$OH)(PPh$_2$O)PtH(P-(cyclohexyl)$_3$). After 60 minutes a conversion was obtained of 81% with a selectivity of 59%.

Example 22

The method of Example 21 was repeated except that carbon monoxide was additionally supplied at a pressure of 2 bar. The selectivity increased to 98%, at 120° C., and at 17% conversion after one hour.

Example 23 to 25

Hydrogenation of 6-methyl-5-hepten-2-one was carried out with the catalysts and conditions of Examples 19 to 22.

| Example | Time Minutes | Conversion % | Selectivity % |
|---|---|---|---|
| 23 | 100 | 17 | 59 |
| 24 | 150 | 9 | 61 |
| 25 | 140 | 14 | 61 |

We claim:

1. A process for the preparation of alcohols, which comprises contacting and reacting hydrogen with a carbonyl reactant comprising one or more compounds selected from the group consisting of aldehydes of the formula R$^3$CHO and ketones of the formula R$^3$COR$^4$, wherein R$^3$ and R$^4$ each is independently selected from the group consisting of substituted and unsubstituted alkyl, alkenyl, cycloalkyl and cycloalkenyl moieties having from 1 to about 10 carbon atoms or a phenyl group, in the presence of a catalyst system comprising a platinum compound, an acid having a pKa in the range of from about 2 to about 10.5 and a phosphorus compound of the formula R$^1$R$^2$POH, wherein R$^1$ and R$^2$ each independently represents a C$_1$ to C$_{10}$ alkyl group or a phenyl group, at a temperature in the range from about 20 to about 150° C. and at a pressure in the range from about 1 to about 100 bar.

2. The process of claim 1, wherein the carbonyl reactant contains one or more compounds having a non-conjugated carbon-carbon double bond.

3. The process of claim 1, wherein the carbonyl reactant comprises one or more aldehydes.

4. The process of claim 1, the platinum compound is selected from the group consisting of platinum bis(cyclo-octa-1,5-diene), platinum acetate and platinum tris-(ethylene).

5. The process of claim 1, wherein the acid having a pKa in the range from about 2 to about 10.5 is a carboxylic acid.

6. The process of claim 5, wherein the carboxylic acid is selected from the group consisting of ethanoic acid, propanoic acid, 2-methylpropanoic acid and butanoic acid.

7. The process of claim 1, wherein the phosphorous compound is diphenylphosphinous acid.

8. The process of claim 1, wherein the temperature is in the range from about 80 to about 120° C.

9. The process of claim 1, wherein the partial pressure of hydrogen is in the range from about 20 to about 60 bar.

10. The process of claim 1, wherein the molar ratio of phosphorus compound to platinum compound is in the range from about 1:1 to about 4:1.

11. The process of claim 1, wherein the molar ratio of acid having a pKa in the range from about 2 to about 10.5 to platinum compound is in the range from about 1:1 to about 100:1.

12. The process of claim 1, wherein toluene is present as a solvent.

13. The process of claim 1 wherein the temperature is in the range from about 80 to about 120° C. and the partial pressure of hydrogen is in the range from about 20 to about 60 bar.

14. The process of claim 13, wherein the acid having a pKa in the range from about 2 to about 10.5 is a carboxylic acid.

15. The process of claim 14, wherein the molar ratio of phosphorus compound to platinum compound is in the range from about 1:1 to about 4:1.

16. The process of claim 15, wherein the molar ratio of carboxylic acid to platinum compound is in the range from about 1:1 to about 100.1.

17. The process of claim 16, wherein the platinum compound is comprises one or more aldehydes.

18. The process of claim 17, wherein the platinum compound is selected from the group consisting of platinum bis(cyclo-octa-1,5-diene) platinum acetate and platinum tris(ethylene).

19. The process of claim 14, wherein the carboxylic acid is selected from the group consisting of ethanoic acid, propanoic acid, 2-methylpropanoic acid and butanoic acid.

20. The process of claim 19, wherein the carbonyl reactant contains one or more compounds having a non-conjugated carbon-carbon double bond.

21. A process for the preparation of alcohols, which comprises contacting and reacting hydrogen with one or more aldehydes of the formula $R^3CHO$, wherein $R^3$ is selected from the group consisting of substituted and unsubstituted alkyl, alkenyl, cycloalkyl and cycloalkenyl moieties having from 1 to about 10 carbon atoms and a phenyl group, in the presence of a catalyst system comprising a platinum compound, a carboxylic acid having a pKa in the range of from about 2 to about 10.5 and a phosphorus compound of the formula $R^1R^2POH$, wherein $R^1$ and $R^2$ each independently represents a $C_1$ to $C_{10}$ alkyl group or a phenyl group, at a temperature in the range from about 80 to about 120° C. and at a partial pressure of hydrogen in the range from about 20 to about 60 bar.

22. The process of claim 21, wherein $R^1$ and $R^2$ each represent phenyl groups and the molar ratio of the phosphorus compound to the platinum compound is in the range from about 1:1 to about 4:1.

23. The process of claim 22, the molar ratio of carboxylic acid to platinum compound is in the range from about 1:1 to about 100:1.

24. The process of claim 23, wherein the platinum compound is selected from the group consisting of platinum bis(cyclo-octa-1,5-diene), platinum acetate and platinum tris(ethylene), the carboxylic acid is selected from the group consisting of ethanoic acid, propanoic acid, 2-methylpropanoic acid and butanoic acid, and the phosphorus compound is diphenylphosphinous acid.

25. The process of claim 24, wherein one or more of the aldehydes contain a non-conjugated carbon-carbon double bond.

* * * * *